(12) United States Patent
Yim (10) Patent No.: US 11,191,862 B2
(45) Date of Patent: Dec. 7, 2021

(54) AIR STERILIZER

(71) Applicant: WELLIS CO. LTD., Seoul (KR)

(72) Inventor: Noh-Bin Yim, Seoul (KR)

(73) Assignee: WELLIS CO. LTD., Seoul (KR)

( * ) Notice: Subject to any disclaimer, the term of this patent is extended or adjusted under 35 U.S.C. 154(b) by 0 days.

(21) Appl. No.: 15/743,753

(22) PCT Filed: Oct. 16, 2015

(86) PCT No.: PCT/KR2015/010934
§ 371 (c)(1),
(2) Date: Jan. 11, 2018

(87) PCT Pub. No.: WO2017/010616
PCT Pub. Date: Jan. 19, 2017

(65) Prior Publication Data
US 2018/0200401 A1    Jul. 19, 2018

(30) Foreign Application Priority Data

Jul. 11, 2015  (KR) .................. 10-2015-0098722

(51) Int. Cl.
*A61L 9/12* (2006.01)
*A61L 9/015* (2006.01)
(Continued)

(52) U.S. Cl.
CPC ............ *A61L 9/122* (2013.01); *A61L 2/0023* (2013.01); *A61L 9/015* (2013.01); *A61L 9/046* (2013.01)

(58) Field of Classification Search
CPC ........ A61L 9/122; A61L 2/0023; A61L 9/046; A61L 9/015
See application file for complete search history.

(56) References Cited

U.S. PATENT DOCUMENTS

2006/0233683 A1* 10/2006 MacDonald .............. A61L 2/20
422/186.07
2010/0122713 A1* 5/2010 Tanaka ................... A23B 7/152
134/26
(Continued)

FOREIGN PATENT DOCUMENTS

GB    2 406 275    3/2005
JP    2002-282346    10/2002
(Continued)

OTHER PUBLICATIONS

International Search Report for International Application No. PCT/KR2015/010934, dated Apr. 15, 2016.

*Primary Examiner* — Sean E Conley
*Assistant Examiner* — Brendan A Hensel
(74) *Attorney, Agent, or Firm* — Kile Park Reed & Houtteman PLLC (57) ABSTRACT

Air sterilizer generates ozone through ozone-generating part and control unit thereof, supplies ozone through air circulating fan, makes air flow by separate fan, and supplies hydrogen peroxide or limonene solution provided in cartridge type and vaporized. Air path is designed such that flow of ozone and flow of air of hydrogen peroxide or limonene solution are designed to maintain laminar flow state for smooth supply of the generated particles, turbulence inducing path for making turbulence easier when two streams meet each other is provided, separate air mixing space is created to create turbulent flow so that ozone and hydrogen peroxide, or ozone and limonene solution generate sufficient chemical reaction in this space to make OH radicals, and laminar flow path for spreading radicals or negative ions is provided, thereby sterilizing and purifying bacterial or indoor air suspended in air by the same principle as in the natural world.

7 Claims, 11 Drawing Sheets (51) Int. Cl.
*A61L 2/00* (2006.01)
*A61L 9/04* (2006.01)

(56) References Cited

U.S. PATENT DOCUMENTS

| | | | | |
|---|---|---|---|---|
| 2010/0243754 A1* | 9/2010 | Harris | ............... | A01M 1/2033 |
| | | | | 239/34 |
| 2011/0171090 A1* | 7/2011 | Johnson | ............... | F24F 3/166 |
| | | | | 423/210 |
| 2013/0320574 A1* | 12/2013 | Sickinger | ............... | A61L 9/032 |
| | | | | 261/141 |
| 2014/0079597 A1* | 3/2014 | Segura Rius | ........... | A61L 9/015 |
| | | | | 422/123 |
| 2016/0216712 A1* | 7/2016 | Baumgartner | ............ | A61L 2/22 |

FOREIGN PATENT DOCUMENTS

| | | |
|---|---|---|
| JP | 2008-125742 | 6/2008 |
| JP | 2013-132418 | 7/2013 |
| KR | 10-1997-0706850 | 12/1997 |
| KR | 10-2003-0036134 | 5/2003 |
| KR | 10-2015-0010009 | 1/2015 |
| KR | 10-1555814 | 9/2015 |

\* cited by examiner

Laminar Flow Part    Turbulence Part (Reaction Part)

FIG. 11B

Laminar Flow Part    Turbulence Part (Reaction Part)

FIG. 11C

High Angle of Attack, Separated Flow

AIR STERILIZER

TECHNICAL FIELD

The present invention relates to an air sterilizer having a hydroxyl radical generator, and more particularly to an air sterilizer capable of most effectively removing air pollutants and germs such as carbon monoxide, sulfur dioxide, nitrogen dioxide, and the like by embodying an air sterilizer having a most suitable condition for generation of a hydroxyl radical (OH), thereby generating a maximum hydroxyl radical per unit time.

BACKGROUND ART

As industrialization progresses and urbanization and population densification accelerate, the problem of air pollution, which human beings need to breathe every day is becoming more and more serious. Fossil fuels that human beings use every day are inevitably releasing pollutants harmful to humans into the air, and pathogenic fine substances such as viruses and germs are also increasing in the air, so that the desire of humans who want to breath clean air becomes stronger. The device used to meet this need is an air purifier or air sterilizer.

Most of the contaminants in the air are inhaled into humans through respiration and cause various diseases. So far, it has been known that the most important role in the natural purification process of pollutants is 'hydroxyl radical (OH)'. The hydroxyl radical (OH) is a major cleansing agent in the atmosphere that removes various pollutants such as carbon monoxide, sulfur dioxide, and nitrogen dioxide. The OH (hydroxyl) radical present in nature is known to be present in the air at a density of 2 hundreds to 20 million (per 1 cc of air, per second).

In general, air purifiers or sterilizers, which are currently in wide use, can be roughly classified as follows. First, it corresponds to the most commonly used method in which the air in the purification space is sucked and passed through the filter, and the contaminants in the air are adsorbed or decomposed by the filter. This method has a problem that reliability of the air cleaning ability by this method is not high because the maintenance characteristic must be performed (that is, a filter must be regularly exchanged with a new filter) when using for a long time and the characteristics of the filter are not perfect.

The second method is increasing ion concentration in the air by using an ion generating device. The air purifier using the ion generating device generates only negative ions so that purification and disinfection by negative ions can be expected to some extent. However, there is a problem that the amount of negative ion generation is not precisely known and the effect associated with the active removal of airborne bacteria in the air is not so high.

The third method uses a Plasma Cluster Ion (PCI) technology. In the PCI technology, plasma ion cleaning technology using a plasma charge is used to generate negative ions and positive ions with air, and through the reaction, the harmful substances are decomposed or inactivated to purify the air. However, the air purification process by this method has not yet been able to accurately identify the chemical mechanism of the PCI behavior, and since the reliability of the sterilization effect is low because it cannot accurately analyze the ion generation amount, the positive and negative effects are not completely clear from the microbiological point of view.

Representative prior art documents related to air sterilizer are as follows.
British laid open patent number GB 2406275 A1 (2005 Mar. 30)
Japanese laid open patent number JP 2002-282346 A (2002 Oct. 2)

DETAILED DESCRIPTION OF THE INVENTION

Objects of the Invention

Generally, the air sterilizer generates ozone, and vaporizes limonene or hydrogen peroxide to generate OH radicals through the chemical reaction thereof, and sterilizes the air using the generated OH radical. In the prior art, the shape of path in the sterilizer, the condition of flow form of ozone and limonene, maximum amount of radical through the conditions thereof, and combination ratio of the ozone and limonene in the condition of the maximum amount are not precisely known.

Therefore, until now, ozone was generated through the generator, the ozone was roughly is transferred through the blower, and the ozone was reacted with limonene to produce an OH radical, without precise recognition of the conditions under which the amount of radical generation is maximum and the shape of the flow path. Therefore, the sterilizer has been designed considering only exterior shape.

The ion generating device of the present invention is characterized in having a high-voltage DC power supply for supplying a DC voltage for generating ozone to the generating part, and an air blower for forcibly blowing ozone generated from the generating part. According to the generating device, a DC voltage can be applied to the generating part from a high-voltage DC power supply, and ozone generated from the generating part can be chemically reacted with the vaporized limonene or hydrogen peroxide to generate OH radical, and OH radicals cab be sent to a wide range of air by a blower. By the action of this OH radical, bacteria floating in the air can be sterilized.

In addition, the air conditioning apparatus of the present invention is characterized in having an inlet for inhaling air, an outlet for discharging ozone generated from the generating part to the laminar flow by a blower together with the air sucked from the inlet, an outlet discharging vaporized limonene (or hydrogen peroxide) by a blower, a reaction space disposed in an airflow path between the inlet and the output, in which the vaporized limonene (or hydrogen peroxide) is reacted in turbulence type that makes the reaction easy, and a laminar flow air flow system disposed after the reaction space and discharging OH radical into a space for actual air purification.

The air conditioning apparatus is a device that applies a DC voltage from the high-voltage DC power supply to an ozone generating part, reacts ozone generated from the generating part with limonene (or hydrogen peroxide) to generate OH radical, and sends the OH radical to a wide range of air by an air blower. By the action of this OH radical, bacteria floating in the air can be sterilized. Further, as the air is circulated, dust, odor and odor components contained in the air are removed by OH radicals. As a result, a pleasant and clean living environment can be realized.

Technical Solution

The present invention relates to an air sterilizer having a most suitable condition capable of generating a maximum amount of OH radicals, which has been derived to solve the problems of air sterilizers using the conventional method.

The air sterilizer according to the present invention generates ozone and vaporizes hydrogen peroxide or limonene solution (olefen) to react with the ozone to generate an OH (hydroxyl) radical and emits the generated radical far away, so that bacteria or indoor air floating in the air are sterilized and purified by using purification principle of nature. The sterilization apparatus according to the present invention generates an ozone in a range of 0.0001 g to 0.5 g per hour at a position 5 cm away from the point of occurrence thereof, vaporizes the limonene or hydrogen peroxide in the range of 0.001 to 0.1 g per hour through air blowing, and generates OH (hydroxyl) radicals by the reaction of hydrogen peroxide with ozone in a range of 500,000 to 20,000,000 numbers/second, and generates OH (hydroxyl) radicals of 85.68% by volume (0.8568 moles) by reacting 1 mole of ozone and 1 mole of limonene, and the sterilizer generates OH (hydroxyl) radicals within the range of 0.3~5:1 ratio of ozone evaporation amount and limonene evaporation amount, and in the optimum range of 0.8:1 ratio of ozone and limonene (ppm basis), 1:3.55 ratio of ozone and limonene (mass basis), and since limonene has a molecular weight of 136.24 and ozone of 48, the air sterilizer which reacts with limonene 0.1 to 1.76 at a ratio of ozone 1 in a mass ratio, is provided.

The air sterilizer according to the present invention generates ozone through an ozone-generating part and a control unit thereof, supplies the ozone through an air circulating fan, makes an air flow by a separate fan, and supplies hydrogen peroxide or a limonene solution (olefen) which are provided in a cartridge type and vaporized. The air path is designed such that the flow of ozone and the flow of air of hydrogen peroxide or limonene solution (olefen) are designed to maintain the laminar flow state for smooth supply of the generated particles, a turbulence inducing path for making turbulence easier when two streams meet each other is provided, a separate air mixing space is created to create a turbulent flow so that ozone and hydrogen peroxide, or ozone and limonene solution (olefen) generate sufficient chemical reaction in this space to make OH (hydroxyl) radicals, and laminar flow path for spreading the radicals or negative ions is provided, thereby sterilizing and purifying bacterial or indoor air suspended in the air by the same principle as in the natural world.

In addition, the air flow path is designed to control the flow rate of the ozone, so that 100,000 to 10 million or more number of negative ions are generated, and 0.001 to 0.05 ppm or less of ozone are generated at a distance of 5 cm from a spill point, and the resulting hydroxyl (OH) radicals or ions are generated in the range of 100,000 to 20,000,000 numbers or more.

Advantageous Effects

According to the air sterilizer of the present invention, it is possible to apply a direct current voltage from the high-voltage DC power supply to an ozone-generating part to react ozone generated by the generating part with limonene (or hydrogen peroxide), and to generate OH radicals, so that the amount of hydroxyl radicals generated can be maximized by accurately controlling the amount of ozone that reacts with the limonene as an apparatus. Thus, the air purification function and the sterilizing function can be effectively performed, thereby realizing a pleasant and clean living environment.

MODE FOR INVENTION

While the present invention has been described in connection with certain embodiments, it is obvious that the invention is not limited to the disclosed embodiments, but, on the contrary, is intended to cover various modifications and similarities. It should be understood, however, that the invention is not intended to be limited to the specific embodiments, but includes all modifications, equivalents, and alternatives falling within the spirit and scope of the invention.

In the following description of the present invention, a detailed description of known related arts will be omitted when it is determined that the gist of the present invention may be unnecessarily obscured. Further, numerals (e.g., first, second, etc.) used in the description of the present invention are merely an identifier for distinguishing one component from another. Also, in this specification, when an part is referred to as "being connected" or being coupled" to another part, it is to be understood that one part may be directly connected or coupled to another part or connected or coupled via another component in between unless a opposite description is present.

Figure 1:
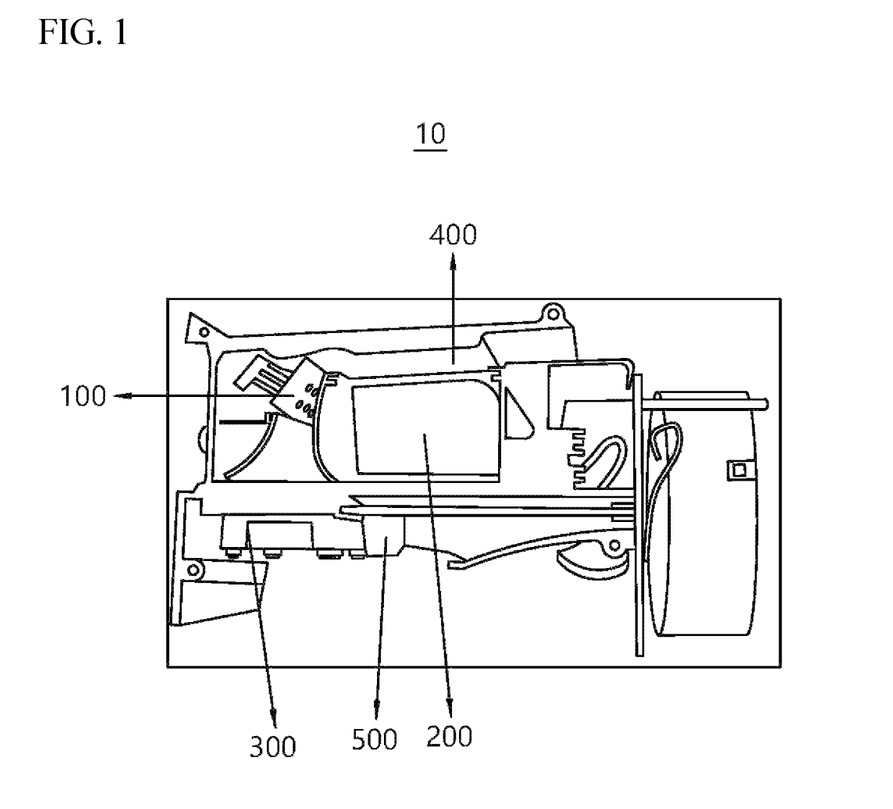
FIGS. 1 and 2 are cross-sectional views of an air sterilizer of the present invention.

According to an embodiment of the present invention, as shown in FIG. 1, the air sterilizer 10 allows the ozone particles to mix well with the limonene or hydrogen peroxide vaporized particles to ensure a continuous chemical reaction, and the air sterilizer 10 includes an ozone-generating part 100 for generating ozone particles through electrodes, an electronic device part 500 having a high-voltage power supply circuit part and a control part thereof, a solution-supply part 200 comprising a container for containing a solution of limonene or hydrogen peroxide and a cover for vaporizing the solution, an inhaling fan for vaporizing the solution and chemical reaction, and a flow path part 400.

Figure 2:
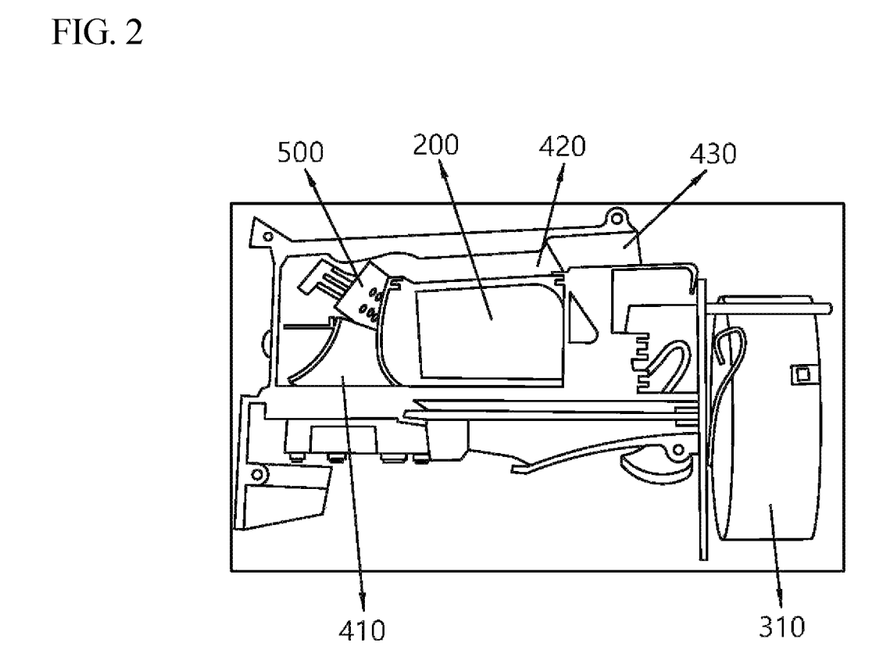
Figure 3:
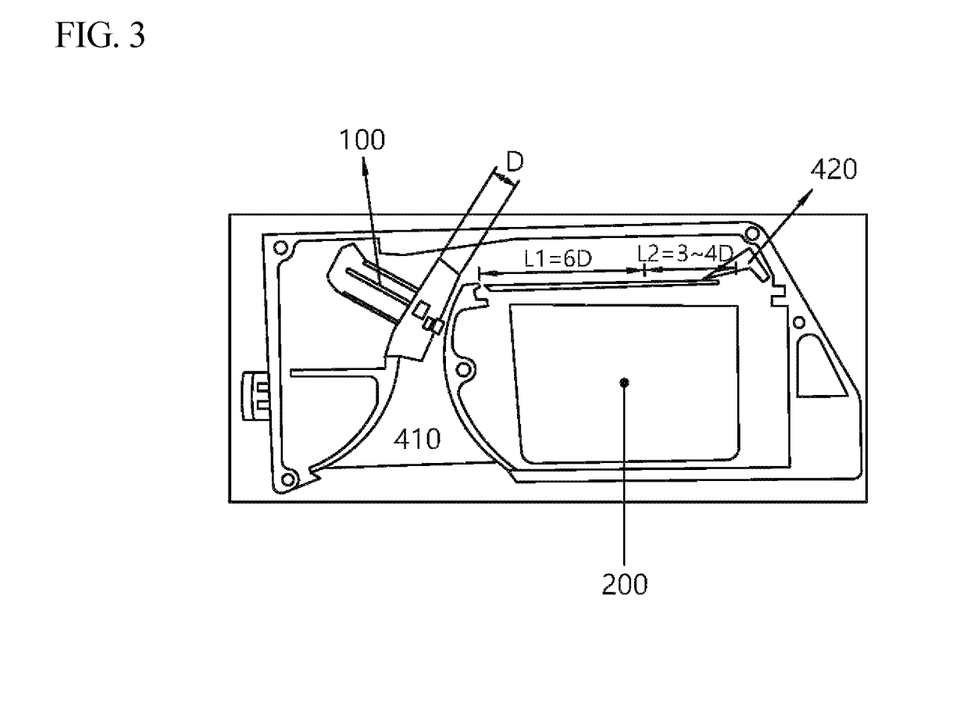
FIG. 3 is a view showing a flow path shape of the air sterilizer of the present invention.
Figure 4:
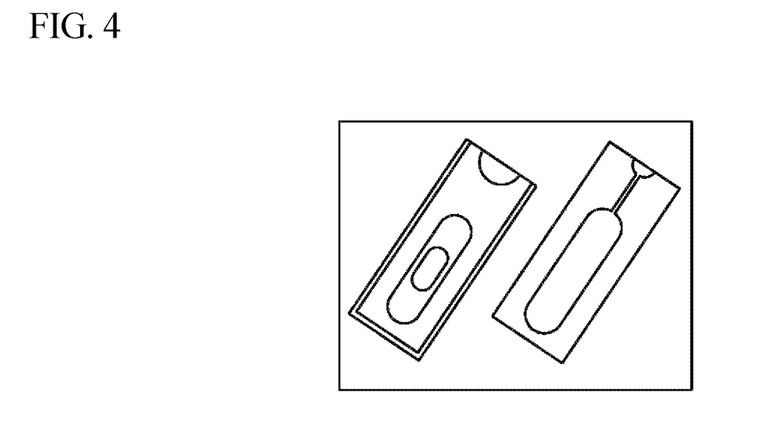
FIGS. 4 and 5 are views showing upper and lower electrodes and an electrode part in the ozone generating part of the present invention.
Figure 5:
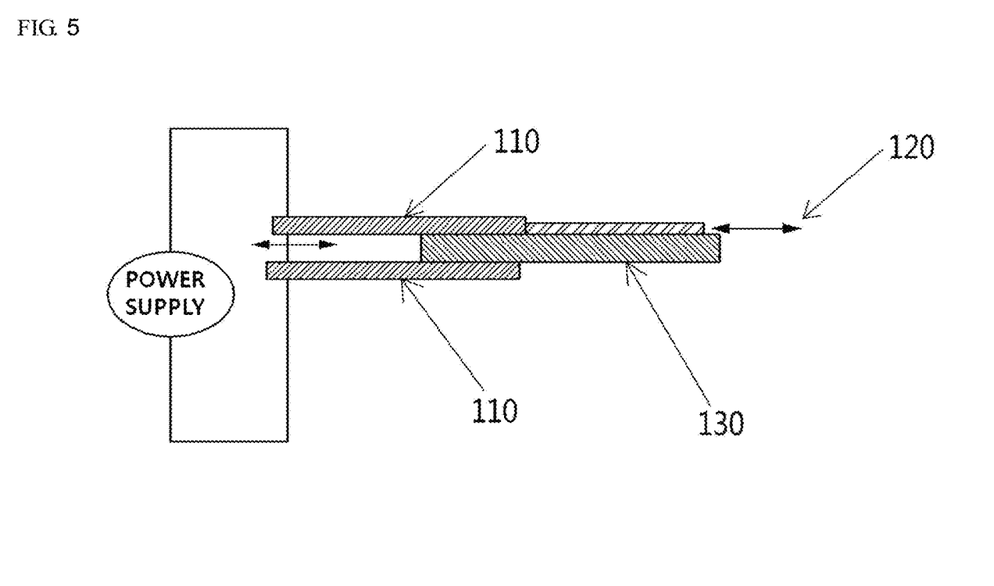

As shown in FIG. 2, the air sterilizer is formed such that the ozone particles generated in the ozone-generating part 100 are mixed well with the vaporized particles of limonene or hydrogen peroxide generated in the solution-supply part 200. It is important to design the flow path so that the flow of the particles becomes laminar flow by placing the laminar flow generating part 410 in order to continuously generate particles from the ozone generating part 500 with a constant flow. It is advantageous to make the turbulence flow by placing the turbulence generating unit 420 before the reaction takes place for a smooth chemical reaction, and a reaction space 430 in which the ozone and the vaporized particles react with each other is located at the downstream end of the turbulence generating unit.

After OH radical is generated by forming a turbulence generating structure (for example, an aerofoil structure) and a turbulent chemical reaction space in a specific space inside the flow path, it is necessary to design the flow path so that a laminar flow occurs again, since it is necessary to transport the OH radicals outside the device as far as possible. In addition, a plurality of fans are required for the air flow of the flow path, a inhaling fan 300 is required to generate an air flow for the solution evaporation of limonene or hydrogen peroxide, and an exhaling fan 310 is required to make laminar flow after ozone particles and solution evaporation particles of limonene or hydrogen peroxide are generated, and to spread OH radicals generated by chemical reaction thereof as far as possible out of the air sterilizer in order to achieve the purifying action of the air, which is the end result of the apparatus.

Generally, the occurrence of laminar flow and turbulence is bounded by a dimensionless variable called Reynolds number, and in the case of flow in a circular pipe, the Reynolds number of the laminar flow is about 2,300 or less.

$$\mathrm{Re} = \frac{\rho v_s^2 / L}{\mu v_s / L^2} = \frac{\rho v_s L}{\mu} = \frac{v_s L}{\nu} = \frac{\text{Inertial forces}}{\text{Viscous forces}}$$

(Where v is the mean velocity of the flow, L is the characteristic length, u is the dynamic viscosity of the fluid, v is the kinematic viscosity of the fluid, ρ is the density of the fluid)

Therefore, it is necessary to design and analyze the flow path so that the Reynolds number becomes 2000 or less. When the diameter of the flow path is simply D, it is known experimentally that laminar flow occurs when the rear distance of the flow path is 6D or more. According to this standard, a design example of the flow path having the occurrence of laminar flow is as follows.

TABLE 1

| Diameter of the channel (mm) | Minimum length of flow path for laminar flow generation (mm) |
|---|---|
| 10 | 60 |
| 15 | 90 |
| 20 | 120 |

In order to generate laminar flow after the fan is installed, an electrode part that generates ozone and a solution vaporization part of limonene or hydrogen peroxide are located behind 6 times of the finally determined diameter of the flow path. Also, after the particles are supplied smoothly through the laminar flow, the flow must be changed to turbulent flow for chemical reaction. For this purpose, the following aerofoil structures are designed in the flow path to induce the generation of turbulence. Since lift and drag may occur depending on the shape of the aerofoil, it is designed considering this (referring to FIGS. 11A and 11B).

In fact, the following streamlined aerofoil structure is inserted in the flow path, thereby inducing the generation of turbulence according to an angle from the rear end of the aerofoil. Alternatively, separate air can be blown into the flow path at a certain angle for the generation of turbulence (referring to FIG. 11C).

After OH radicals are generated by the chemical reaction, it is effective to purify the air sterilization effectively that the generated OH radicals are discharged to the outside of the apparatus as far as possible. Therefore, the air flow is designed to change air flow to laminar flow and to increase velocity of air. To this end, a separate fan may be installed or an air flow may be generated. The designed flow path and its function are shown in FIG. 3.

The structure of the ozone generating electrode in the ozone-generating part and the cartridge containing the limonene (or hydrogen peroxide) solution in according to the present invention has a cross-sectional view as shown in FIG. 3. That is, air is introduced through a inhaling fan (not shown) provided at the lower part, and the introduced air passes through the central part of limonene (or hydrogen peroxide) solution evaporation center spaced apart by L1=6D through an air path of which size is D to make laminar flow to satisfy condition of evaporation. In addition, after the evaporation has occurred well, since turbulence is generated at a position spaced apart more by L2=3~4D (total distance 9~10D from the beginning of the flow), so an airfoil structure for generating turbulence is provided at this position, and a reaction space structure is disposed downstream to make sure that the solution and ozone are well mixed. Since it is good for air sterilizing and purifying that the OH radical generated after the sufficient reaction occurs in the reaction space 430 is discharged to the outside of the apparatus as far as possible, an additional fan may be installed or an air flow may be generated such that the air flow is changed again to the laminar flow and the center air speed is increased.

The ozone-generating part 100 of the present invention includes a ceramic electrode 110 divided into upper and lower parts as shown in FIG. 4. The ceramic electrode 110 has a small size and a long service life, and generates ozone by 0.1 mg/h to 1 g/h. The amount of generation is determined by the voltage and current applied to both ends of the electrode, the area of the electrode, etc. In order to precisely control and manage the generated amount, the mechanical movement and the generation of the amount are controlled. Voltage control uses a high voltage of 2000 to 7000 V, and in the case of ozone, it is supplied in the form of a pulse wave with a frequency of 1,000 to 100,000 Hz.

The amount of ozone generation is possible by controlling the voltage, but the precise control is not possible. Therefore, the present invention uses controlling the reaction length or the area of both sides of the ceramic electrode, while maintaining the voltage in constant to control the amount of ozone generation precisely through the control of current and power. This ozone generation amount control is performed through the electrode structure as shown in FIG. 5.

Ceramic electrodes 110 are placed on upper and lower parts of the slide reference plate 130, one of the ceramic electrodes is mechanically and finely transferred through the electrode position adjusting part 120. Accordingly, the amount of ozone generated is measured at a predetermined distance through a meter or a sensor, and when the desired amount of generated ozone is reached, the adjusting position is finished and the position is fixed by bonding or the like. Later, the desired amount of generated ozone can be obtained at the position repeatedly. There are various methods for adjusting the electrode position, but the simplest method employs a mechanical precision screw, adopts a spring structure in the direction opposite to the screw direction, and enables the fine distance to be transferred by the rotation of the screw. The electrode is not only in the form of a plate but also in the form of a rod, and it is possible to finely control the generation amount by controlling the area of the electrode.

According to the present invention, when the amount of ozone discharged without reacting with the reaction gas is detected, it means that the ozone and the limonene (or the hydrogen peroxide) do not react at a proper ratio and the amount of ozone is excessively large. Therefore, it is necessary to preliminarily experiment with various predetermined conditions and apply it as a data table to control the condition. Alternatively, an ozone sensor or an ozone detector may be installed at the exit of the apparatus, through which of OH (hydroxyl) radical is discharged, and the conditions are adjusted so that the detection amount becomes zero. This is a method used to control the condition (air volume, amount of ozone generation, amount of limonene, air velocity, etc.) of the mass product by the data through the preliminary experiment and to control the conditions for the situation changing by the feedback through the sensor, and a method of actively using the fact that a minute amount of ozone is detected according to the reaction and becomes zero when the complete reaction is performed.

Figure 6:
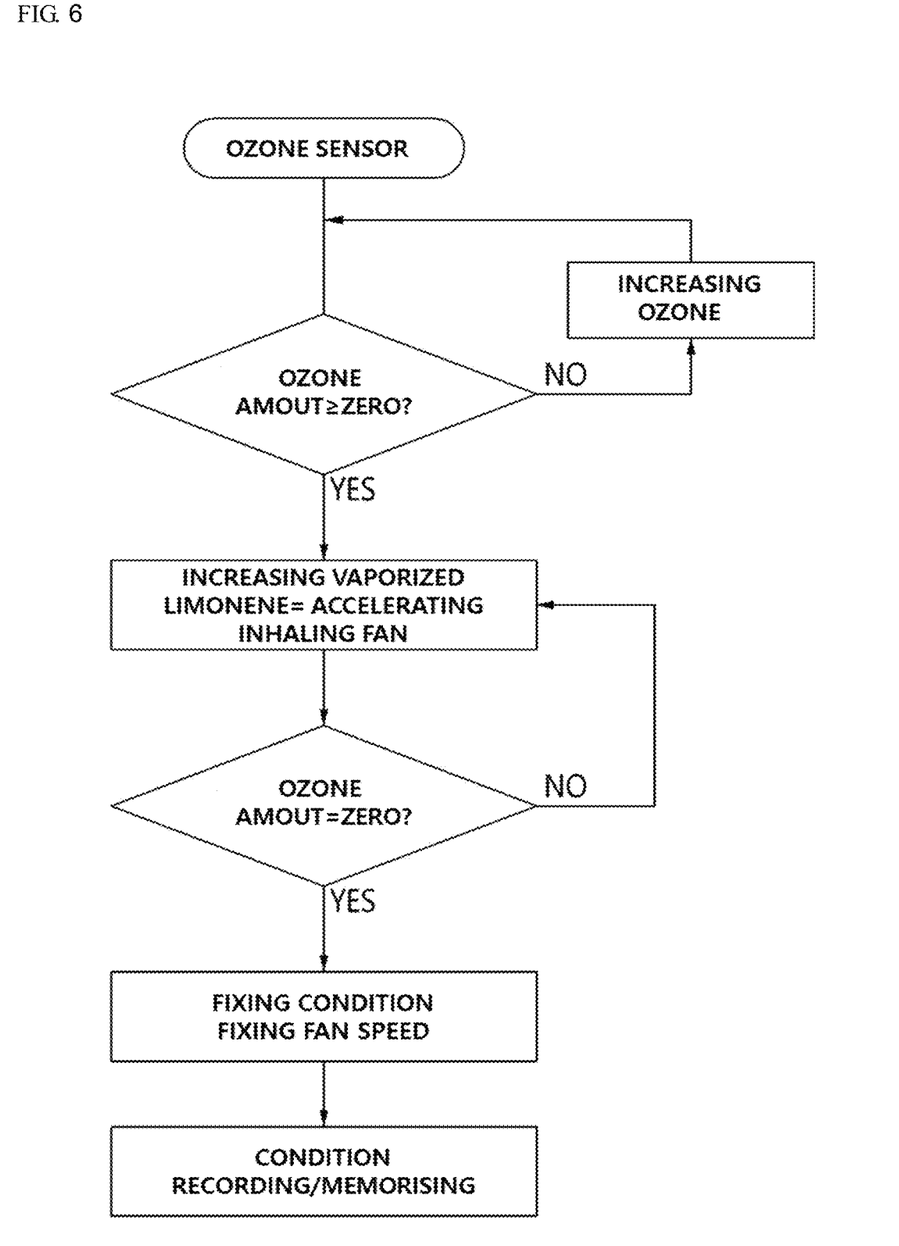
FIG. 6 is a flow chart showing an algorithm for controlling the limonene evolution using the ozone sensor of the present invention.

Referring to FIG. 6, the amount of ozone is measured by an ozone sensor (or a detector) mounted on a device outlet. If it is zero, first, the ozone amount is increased. In order for that, the reaction area of the electrode is increased, or the voltage and current are adjusted. When the amount of ozone becomes zero or more, the evaporation amount of limonene (or hydrogen peroxide) is increased. The concentration of ozone detected by the sensor decreases as the reaction goes on. Each condition (ozone generator electrode position, area, voltage, current, ozone generation amount, limonene vaporization amount, air volume of the suction fan at that time, wind speed, temperature, humidity, etc.) at the moment when the concentration becomes zero is fixed, and the condition may be recorded to be used as a control table for controlling the sterilizer or criteria in production process.

The ozone generation control part increases or decreases the amount of ozone generated by the ozone-generating part driving module or increases or decreases the amount of wind generated by the fan driving module. The amount of ozone generated from the ozone-generating part can be appropriately controlled, for example, by adjusting the generation area of the two electrodes of a discharge unit, adjusting the voltage difference between the electrodes, or the flow rate of air introduced from the fan, so that it be controlled on the basis of the moment when the temperature is zero.

Figure 7:
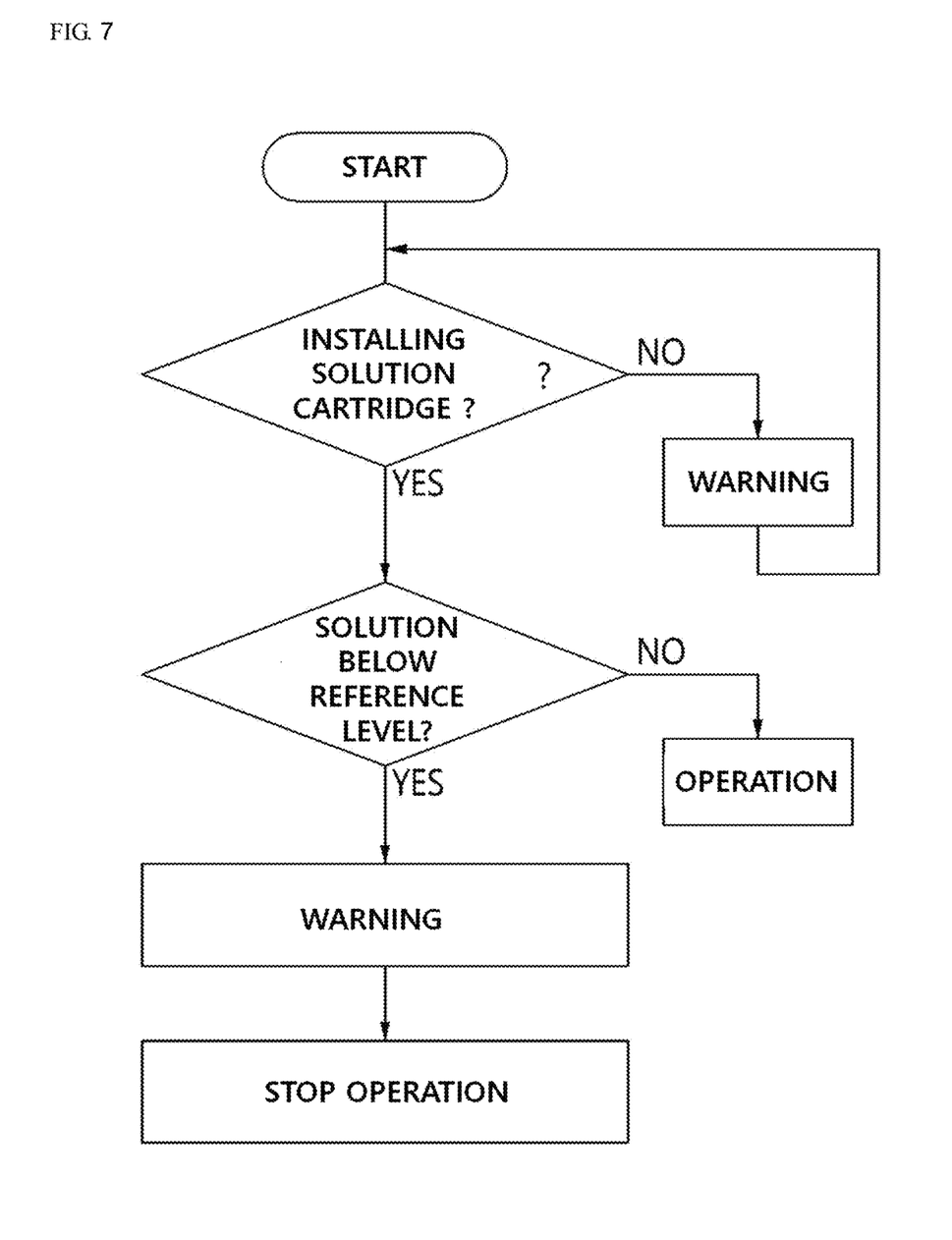
FIG. 7 is a flow chart showing an algorithm through which the solution remaining amount detecting device of the present invention is operated.

Also, the most important factor in the solution-supply part 200 according to the present invention is a method of measuring the amount of solution remaining in the solution cartridge. The solution is limonene or hydrogen peroxide. A structure for electrically or optically sensing is included in the cartridge structure to measure the amount of the remaining solution, and it is determined whether or not the cartridge is normally installed. When receiving a signal indicating that it may be operated by an initial signal generated by a sending structure and circuit for a solution of a certain height at the time of initial setting, making a reference for supplying power, and finally the solution reaching a level below which it needs to be refilled, it is used as a reference to disconnect power. The reason for stopping the power supply is that the ozone-generating part continues to operate even when limonene or hydrogen peroxide is not supplied and the ozone is discharged over a certain amount without reacting with limonene or hydrogen peroxide, which adversely affects the surrounding environment. The algorithm applied in this case is shown in FIG. 7.

That is, the entire operation or power supply for the purpose of the evaporation of the solution of the limonene or hydrogen peroxide to be installed, operates only when the solution is installed and the remaining amount is confirmed to be a predetermined amount or more. If the remaining amount of the solution is less than a predetermined amount, or if the solution is not installed, it does not operate with warning indication. Therefore, it is necessary to provide a method of informing whether the solution is initially installed, and remaining amount or remaining time when the remaining solution becomes a certain amount or less. In the present invention, optical and electric methods can be used.

Figure 8:
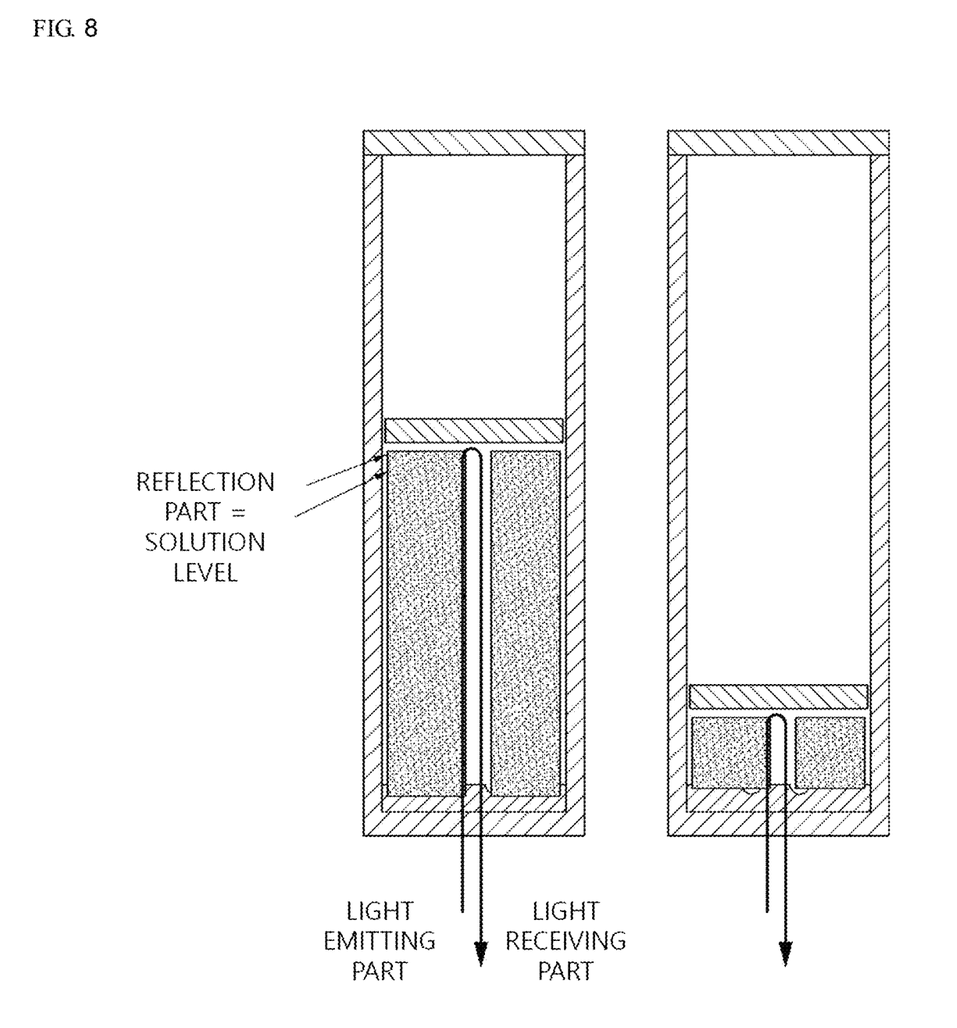
FIG. 8 is a view showing an example embodiment of the optical remaining amount detecting device of the present invention.

The optical residual quantity detection way used in the present invention is as shown in FIG. 8, in which a reflection plate and a reflection part are installed in a solution in the solution cartridge so as to float in the solution, and then a light emitting optical system and a light receiving optical system are provided on the bottom or side. The housing of the cartridge must be made of a material that does not hinder the transmission of light, and the cost of the optical system of the light emitting part and the light receiving part is large. Also, the light source to be used should not be affected by the reciprocation from the solution to at least the reflection part, and it is possible to use the infrared light source with frequency conversion.

It can be determined that the cartridge is present when the light emitted from the light emitting part installed at the main body is reflected by the cartridge and detected by the light receiving part, and the remaining amount of the solution can be detected by sensing amount of light, since the intensity of light passing though the solution decreases as the amount of solution increases. When the light is detected, the algorithm assumes that the solution cartridge is installed, and the light intensity gradually increases with reference to the initial state. If the solution falls below the desired level and the intensity becomes larger than a critical point, it is determined that the solution is insufficient.

Figure 9:
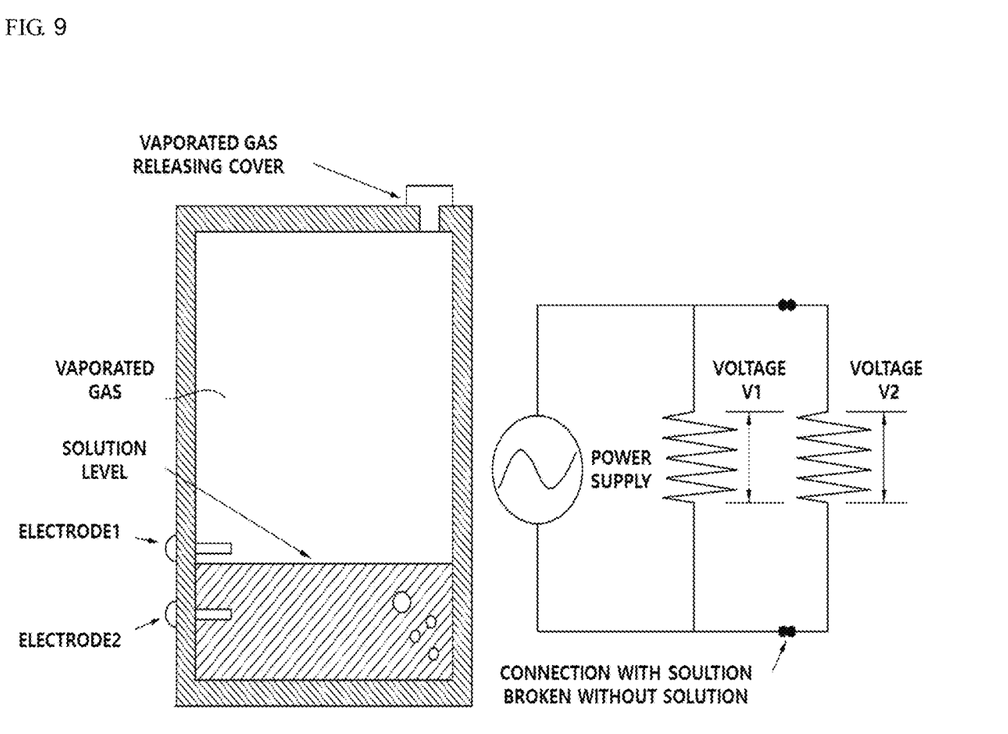
FIG. 9 is a view showing an example embodiment of an electric remaining amount detecting device of the present invention.

The method of detecting the remaining amount through electric type according to the present invention is shown in FIG. 9, in which a plurality of electrodes connected to the outside from the inside of the solution cartridge are installed on the side surface with a different height, a voltage is applied between the electrodes at the side, and an electric circuit for detecting the voltage between the electrodes are provided. If a solution exists between the electrodes, current may flow. An electric circuit is connected to the electrode 1 and the electrode 2 on the cartridge side from the main body. The electric circuit has a structure such that a part of the electric circuit is connected or broken in accordance with the states of the electrodes 1 and 2. That is, if the solution is filled such that a current flows between electrodes 1 and 2, the voltage (V2) appears normally. In this case, the solution is determined to be normal and the sterilizer operates. As the solution is evaporated, the level is lowered and the residual solution is lowered down to the bottom of one of the electrodes so that the solution level is disposed between the electrodes 1 and 2, the solution is not present between the electrodes and the resistance increases sharply so that the current does not flow. In this case, it is judged abnormal and the operation is stopped. Even if the solution cartridge is not initially installed, the resistance is increased, so that no current flows. Therefore, when the voltage (V1) is measured, which is the same as the power source, it is considered that the solution is not filled enough and the generation of ozone is stopped.

Figure 10:
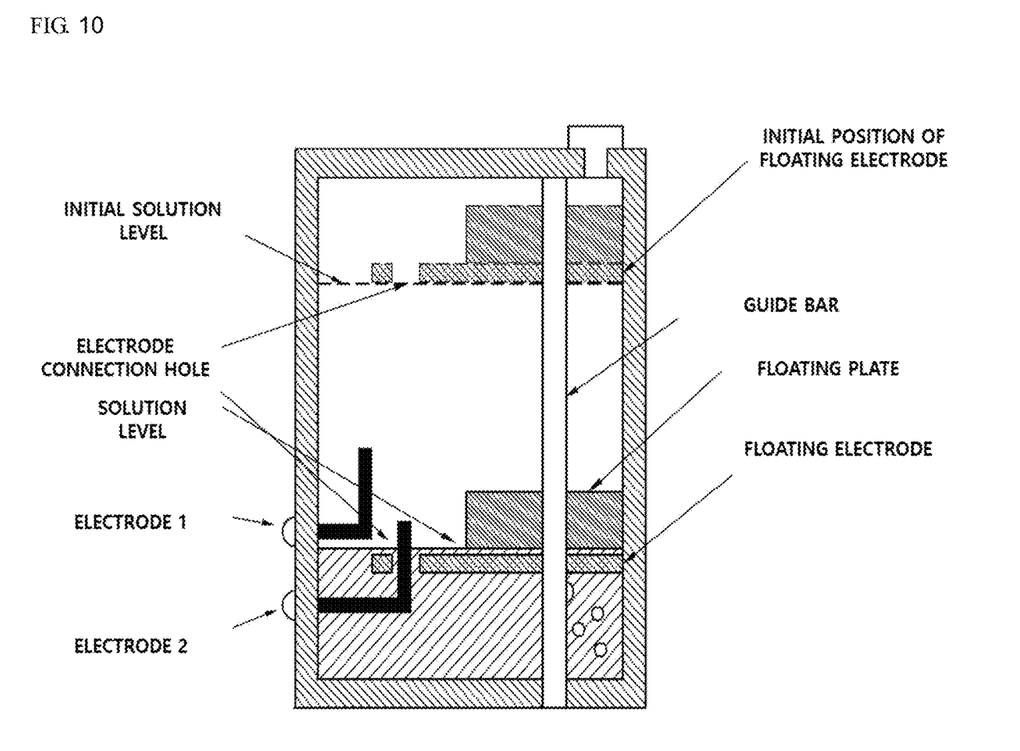
FIG. 10 is a diagram showing an example of the floating electrode type remaining amount detecting device of the present invention.
Figure 11A:
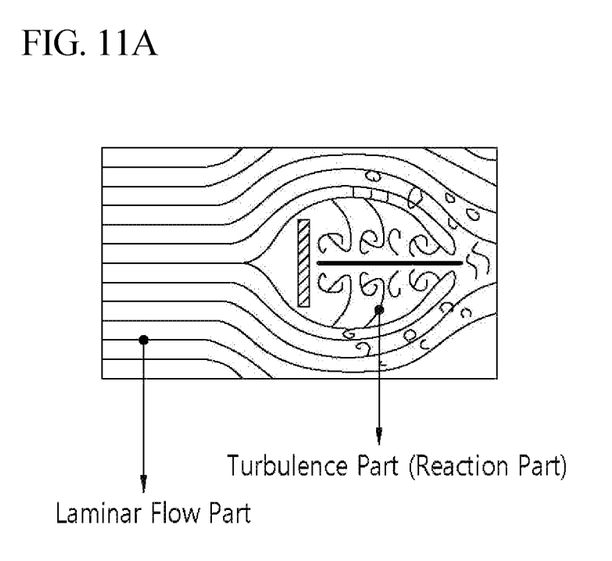
FIGS. 11A, 11B and 11C are schematic cross-sectional views of aerofoil structures according to embodiments of the present invention.
Figure 11B:
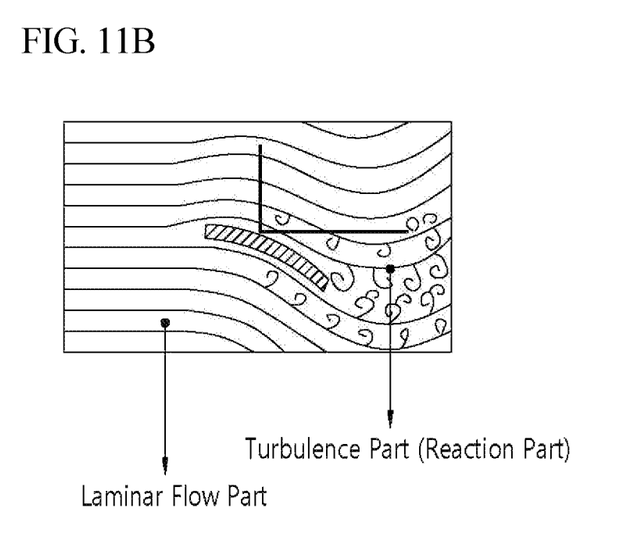
Figure 11C:
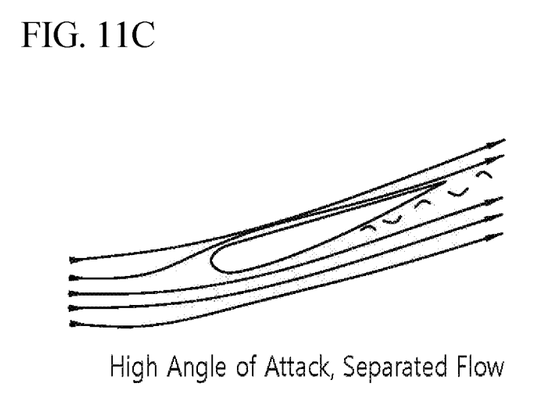

In addition, in the method for detecting the remaining amount of the solution according to the present invention, there is a method of using the floating electrode as shown in FIG. 10 in addition to the optical and electrical method described above. Two electrodes are provided at the same height (height of the electrode 1), and a floating electrode (conductive plate) is disposed on the solution. The floating electrode (conductive plate) is lowered as the solution level decreases. When the solution is reduced by the predetermined position, so that the floating electrode makes contact with the electrode, the level of the floating electrode is determined to be the level of solution. At this time, it is necessary to provide a guide structure (guide rod) so as to find a position where the conductive plate easily touches the electrode. In FIG. 10, two electrodes 1 and 2 are formed at different heights, and the floating plate is on the upper surface of the solution. As the solution is continuously evaporated to reduce its amount, the floating plates is lowered along the guide rod. When the floating plate is inserted into the electrode so that a current flows, the height of the solution can be known.

Hereinafter, the calculation of the molar ratio of the limonene to the ozone necessary for the formation of hydroxyl radicals usable in the present invention will be described. In order to generate OH radicals in the air sterilizer according to the present invention, a chemical reaction of ozone-olefin must be accompanied, a typical olefin is limonene, and the reaction formula thereof is as follows.

Limonene+O3→0.85(0.65CI—CH3-OO*+0.35CI—OO*)+0.15(0.68(CIx-OO*+HCHO)+0.32(keto-limonene+CH2OO*))(wherein O3 refers to ozone)

The substances generated by this reaction generate OH radicals through the following reactions, respectively.

CI—CH3-OO*→0.2(limononic_acid+CH3-OH)+0.2*stabCI—CH3-OO+0.1*7OH-lim+0.5*(0.5*(oxy-lim+XO2+HO2)+0.5(limonic_acid-CO—OO+H—CO—H))+0.9OH+0.01O3P CI—OO*→0.2(C=C7-OO+H—CO—CO—H+XO2)+0.3limononic_acid+0.5stabCI-OO+0.9OH+0.01O3P CIx-OO*→0.15(MCH—OO+CH3-CO—OO.)+0.45(MCH—CH3+CO2)+0.35stabCIx-OO+0.05(keto-limonene+O3P)+0.9OH+0.01*O3P Considering the above formula, when one mole of ozone reacts with one mole of limonene, 0.8568 moles of OH radicals are produced, theoretically. However, this is only the theoretical result. In actual air sterilizer, the amount of OH radical is inevitably changed depending on conditions such as wind speed, flow type and ambient temperature. As a result of the experiment, it was found that the amount of OH radical was maximized when the ratio of limonene to ozone was 1:0.8 as shown in the following experimental data table, and the amount of ozone was 0.6 to 4.2 (OH) radicals, which can bring about the effect of air sterilization, can be generated by the air sterilizer according to the present invention, with respect to amount of one of the limonene. It was found that the optimum ratio of limonene and ozone is 0.6~4.73 to 1 in a mass ratio, since the molecular weight of the limonene is 136.24 and the molecular weight of the ozone is 48. Considering the experimental error, it is considered that it is possible to generate radicals useful for sterilization in an actual sterilizer operation when OH (hydroxyl) radicals are generated as useful numbers within the evaporation ratio of limonene to ozone is 1 to 0.15~6, or mass ratio of limonene to ozone is 1 to 0.05~2.11.

TABLE 2

| | d-limonene(ppm) | O3(ppm) | Aerosol yield (OH Radical) | d-limonene/O3 |
|---|---|---|---|---|
| 1 | 0.65 | 0.81 | 94% | 0.8 |
| 2 | 0.45 | 0.35 | 78% | 1.3 |
| 3 | 0.48 | 0.18 | 77% | 2.7 |
| 4 | 0.143 | 0.239 | 77% | 0.6 |
| 5 | 0.296 | 0.251 | 72% | 1.2 |
| 6 | 0.18 | 0.12 | 68% | 1.5 |
| 7 | 0.63 | 0.3 | 63% | 2.1 |
| 8 | 0.093 | 0.081 | 45% | 1.1 |
| 9 | 0.093 | 0.022 | 43% | 4.2 |

Table: the amount of OH radicals generated by the reaction amount of limonene and ozone (experimental result)

As an example of a system that purifies the air (11 m$^3$/hr) per hour, assuming that the standard of generating OH (hydroxyl) radicals useful for air purification is slightly more than 10 million (per 1 cc and per second), $0^7 \times 11 \times 10^6 \times 3600$ number of OH (hydroxyl) radicals are required (per hour) and $9.5 \times 10^{18}$ number of OH (hydroxyl) radicals are required (per day) since 1 m$^3$ is $10^6$ cc$^2$.

Then, $5.7 \times 10^{20}$ number of OH (hydroxyl) radicals, which is $9.46 \times 10^{-4}$ mol=0.128 g, are required for 60 days. Assuming that the produced limonene reacts with only 1% of the OH radicals in the supplied amount, it is estimated that 12.8 g ($9.456 \times 10^{-2}$ mol) is used for two months. Considering the ozone molecular weight of 48, ozone should be 4.8 g per 2 months and 0.08 g=3.3 mg/hr=$1.54 \times 10^{-6}$ m$^3$ per hour. Only 3.3 mg of ozone is required per hour. Based on the optimal molar ratio of 1:0.8, 2.5 mg/hr of ozone is required regarding to 12.8 g of limonene.

With this approximate range of response predictions, we can predict the amount of blowing, the amount of ozone, and the evaporation amount of limonene (or hydrogen peroxide) at which the optimum reaction can occur, but it is not easy to know the exact process by which the optimum reaction takes place. If the amount of wind, the amount of ozone generated, the amount of limonene evaporation, the structure of the flow path, etc. are changed, other methods should be used to calculate or find out the experiment value. Therefore, the present invention proposes a method for determining optimum conditions for changing conditions by controlling the apparatus by searching for optimal OH (hydroxyl) radical generation conditions.

For limonene which is vaporized by a certain amount of blowing in an approximate range, the amount of ozone generated is added or subtracted, and the amount of generated ozone is measured using an ozone detector or an ozone sensor at the discharge part after the reaction. Before evaporation of limonene, certain amount of ozone is detected, but the amount of ozone decreases to be zero as the limonene is vaporized so that the vaporized limonene reacts with the ozone to generate OH (hydroxyl) radical. At this time, the amount of ozone generated, the amount of limonene vaporized, and the amount of blowing at that time become the most optimal OH (hydroxyl) radical generating conditions. Therefore, the optimum condition can be selected by the feedback data of the ozone sensor or the ozone detector stalled at the discharge part of the apparatus.

Through this process, it was confirmed that the ozone generated in the case of the present invention started to react at about 0.1 ppm before the reaction, then gradually decreased, and when the complete reaction was completed, the amount of ozone reached to 0.000 ppm.

In the present invention, hydrogen peroxide may be used instead of limonene. Hydroxyl radicals are generated through a reaction of hydrogen peroxide and ozone, as follows.

$$H_2O_2 + 2O_3 \rightarrow 2OH + 3O_2$$

That is, when 2 moles (96 g) of ozone reacts with 1 mole (34 g) of hydrogen peroxide, 2 hydroxyl moles are produced. Therefore, a similar amount of ozone is generated in this case, and the amount of hydrogen peroxide to be vaporized is half the amount of ozone by the molar scale (or volume, ppm). Through the same reaction experiment as in the case of limonene, it was confirmed that a useful number of OH (hydroxyl) radicals are generated a within a range of about 0.1~10 ozone amount per 1 mole of hydrogen peroxide. As such, hydrogen peroxide can also generate sufficient amounts of OH radicals for indoor air purification. The condition of the reference instrument can be determined through a reference point at which the amount of ozone detected becomes zero as the method using limonene, described above. Accordingly, in the apparatus constructed according to the present patent, a sufficient number of OH (hydroxyl) radicals are generated under the most optimal conditions, and the produced radicals or negative ions are made to flow far through the laminar flow channel by the air flow of the air circulating fan, so that it is possible to sterilize and purify bacteria or indoor air floating in the air on the same principle as the purification principle of the natural world.

In addition, according to one embodiment of the present invention, a negative ion generating device is additionally provided at the discharge part of the air sterilizer to simultaneously generate an OH (hydroxyl) radical and a negative ion to dissipate in the air, thereby further ensuring air sterilization and purification.

The invention claimed is:

1. An air sterilizer for sterilizing air by generating hydroxyl radicals through reaction of ozone generated from an ozone-generating part with limonene aerosol generated from limonene solution, the air sterilizer comprising:
    a main body;
    an ozone-generating part generating ozone;
    an electronic device part having a power supply circuit part and a control part;
    a solution-supply part for supplying the limonene solution, the solution-supply part being configured to be received into the main body; and
    an inhaling fan attached flow path part comprising a fan housed within the main body,
    wherein the solution-supply part for supplying the limonene solution comprises a solution cartridge including an electrical or optical sensor configured to measure an amount of limonene solution remaining in the solution cartridge,
    the inhaling fan attached flow path part has a length and a cross-sectional diameter, and the length is nine to ten times greater than the cross-sectional diameter,
    an output end of the inhaling fan attached flow path part includes an aerofoil structure downstream of the fan as a turbulence generating structure of the inhaling fan attached flow path part,
    the aerofoil structure housed within the inhaling fan attached flow path part which is housed within the main body, and
    the aerofoil structure is configured to induce turbulence according to an angle from a rear end of the aerofoil.

2. The air sterilizer of claim 1, wherein the ozone-generating part, the electronic device part, the solution-supply part, and the inhaling fan attached flow path part are integrally formed.

3. The air sterilizer of claim 1, wherein the ozone-generating part and the solution-supply part are made of the solution cartridge, which is detachably attached to the main body of the air sterilizer.

4. The air sterilizer of claim 1, wherein the solution cartridge is detachably attached to the main body of the air sterilizer.

5. The air sterilizer of claim 1, further comprising an ozone sensor installed at an outlet of the air sterilizer, wherein an ozone generation amount is controlled by controlling operating conditions of the air sterilizer based on an ozone amount detected by the ozone sensor, wherein the operating conditions include one or more of the reaction length and area of an electrode on both sides of the ozone-generating part, electrode position, area, voltage, current, solution evaporation amount, wind volume of an inhaling fan part of the inhaling fan attached flow path part, wind speed of the inhaling fan part, temperature, and humidity.

6. The air sterilizer of claim 1, wherein the solution-supply part electrically or optically detects remaining amount of the limonene solution to control whether the ozone-generating part operates.

7. An air sterilizer for sterilizing air by generating hydroxyl radicals through reaction of ozone generated from an ozone-generating part with limonene aerosol generated from limonene solution, the air sterilizer comprising:
    a main body;
    an electronic device part having a power supply circuit part and a control part, the electron device part being housed within the main body;
    an ozone-generating part that generates the ozone, the ozone-generating part being housed within the main body;
    a solution cartridge received into the main body, the solution cartridge including the limonene solution and releasing the limonene aerosol, the solution cartridge including a sensor that measures an amount of limonene solution remaining in the solution cartridge; and
    a multi-fan turbulence inducing flow path part housed within the main body and including:
        an input fan at an input end of the multi-fan turbulence inducing flow path part;
        a laminar flow generating part downstream from the input fan, the laminar flow generating part adjacent to the ozone-generating part and the solution cartridge;
        an aerofoil structure housed within the multi-fan turbulence inducing flow path part which is housed within the main body, the aerofoil structure being disposed downstream from the input fan and the laminar flow generating part to generate turbulence to air flow in the multi-fan aerofoil flow path part;
        a reaction space downstream from the aerofoil structure in which the limonene aerosol and the ozone react with each other to generate the hydroxyl radicals; and
        an output fan at an output end of the multi-fan turbulence inducing flow path part to output the hydroxyl radicals,
    wherein the electronic device part controls such that no power is provided for the generating of the ozone in case that the sensor that measures the amount of limonene solution senses that the amount of limonene solution reaches below a level indicating refill of the solution cartridge is necessary, and wherein the aerofoil structure is configured to induce the turbulence to the air flow according to an angle from a rear end of the aerofoil.

\* \* \* \* \*